US00RE39755E

(19) United States
(12) Reissued Patent
Schouteeten et al.

(10) Patent Number: US RE39,755 E
(45) Date of Reissued Patent: Jul. 31, 2007

(54) 3-(1-HYDROXY-PENTYLIDENE)-5-NITRO-3H-BENZOFURAN-2-ONE A PROCESS FOR THE PREPARATION THEREOF AND THE USE THEREOF

(75) Inventors: Alan Schouteeten, Ezanville (FR); Francoise Mordacq, Trosly Breuil (FR)

(73) Assignee: Clariant France, Puteaux (FR)

(21) Appl. No.: 11/050,627

(22) Filed: Feb. 3, 2005

Related U.S. Patent Documents

Reissue of:
(64) Patent No.: 6,515,147
Issued: Feb. 4, 2003
Appl. No.: 09/761,452
Filed: Jan. 17, 2001

(30) Foreign Application Priority Data

Jan. 17, 2000 (FR) ..... 00 00523

(51) Int. Cl.
*C07D 307/83* (2006.01)

(52) U.S. Cl. ..... 549/304; 549/305
(58) Field of Classification Search ..... 549/304, 549/305
See application file for complete search history.

(56) References Cited

U.S. PATENT DOCUMENTS

| | | | | |
|---|---|---|---|---|
| 3,248,401 A | | 4/1966 | Tondeur et al. | |
| 4,252,817 A | | 2/1981 | Closse et al. | |
| 5,223,510 A | * | 6/1993 | Gubin et al. | 514/299 |
| 5,444,056 A | * | 8/1995 | Gubin et al. | 514/183 |
| 5,854,282 A | * | 12/1998 | Mellin | 514/469 |

FOREIGN PATENT DOCUMENTS

WO 96/05190 2/1996

OTHER PUBLICATIONS

EPO Search Report for EP Application No. 01810033, mail date Sep. 6, 2001.

J. N. Chatterjea: Journal of the Indian Chemical Society, vol. 33, No. 3, 1956, p. 175–182.

J. N. Chatterjea: Journal of the Indian Chemical Society, vol. 34, No. 4, 1957, p. 299–305.

Elix et al., Aust. J. Chem. (1973), 26 (J), 1079–91 CAS Abstract.

* cited by examiner

*Primary Examiner*—Kamal S. Saeed
(74) *Attorney, Agent, or Firm*—Anthony A. Bisulca

(57) ABSTRACT

A product corresponding to formula (I) or its ketonic tautomer form (II)

(I)

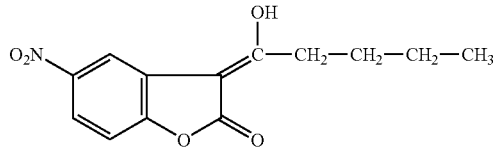

(II)

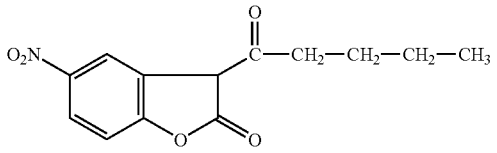

which is 3-(1-hydroxy-pentylidene)-5-nitro-3H-benzofuran-2-one, a process for the preparation and use of the product corresponding to formula (I) or its tautomeric form (II), a process for the preparation and use, particularly for the production of synthesis intermediates.

11 Claims, No Drawings

3-(1-HYDROXY-PENTYLIDENE)-5-NITRO-3H-BENZOFURAN-2-ONE A PROCESS FOR THE PREPARATION THEREOF AND THE USE THEREOF

Matter enclosed in heavy brackets [ ] appears in the original patent but forms no part of this reissue specification; matter printed in italics indicates the additions made by reissue.

The present invention relates to 3-(1-hydroxy-pentylidene)-5-nitro-3H-benzofuran-2-one and to its ketonic tautomer form 3-(1-oxo-pentyl)-5-nitro-3H-benzofuran-2-one.

3-(1-hydroxy-pentylidene)-5-nitro-3H-benzofuran-2-one is a new compound which may be used as a synthesis intermediate. In particular, it may be converted to 2-butyl-5-nitrobenzofuran by hydrolysis, decarboxylation and cyclisation, by simple heating in an acid medium.

2-butyl-5-nitrobenzofuran may act as an intermediate in the synthesis of an antiarrythmic, dronedarone.

The present invention provides, therefore, 3-(1-hydroxy-pentylidene)-5-nitro-3H-benzofuran-2-one corresponding to formula (I)

(I)

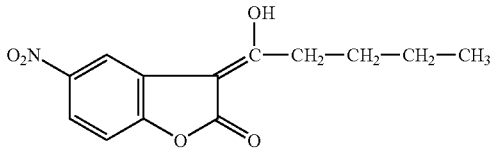

and its ketonic tautomer form, 3-(1-oxo-pentyl)-5-nitro-3H-benzofuran-2-one corresponding to formula (II)

(II)

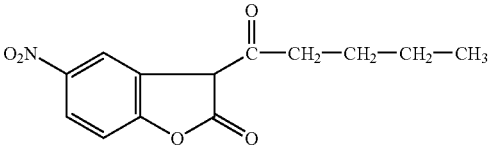

SUMMARY OF THE INVENTION

The present invention also provides a process for the preparation of the compound corresponding to formula (I) and its ketonic tautomer form (II).

Finally, the present invention provides the use of the compound corresponding to formula (I) or its ketonic tautomer form (II) as a synthesis intermediate, particularly for the preparation of active pharmaceutical principles.

DESCRIPTION OF THE PREFERRED EMBODIMENTS

In particular, the present invention provides the compound corresponding to formula (I) and the preparation thereof.

This preparation is characterised in that 5-nitro-3H-benzofuran-2-one is reacted, at a temperature above 30° C., with pentanoic anhydride and a salt of pentanoic acid, optionally in the presence of pentanoic acid, then the resulting reaction mixture is acidified, and then the expected product is isolated.

This method of operating constitutes an improvement to the process described by J. N. Chatterjea, J. Indian Chem. Soc. Vol. 33 no. 3, 1956, p. 175–182 and J. Indian Chem. Soc. Vol. 34, no.4, 1957, p. 299–305.

This improvement to the process relates to the acidification of the reaction mixture at the end of the reaction which allows better isolation of the expected product. A second improvement relates to the reduction in the amount of acid anhydride required for the reaction.

Under preferential conditions for carrying out the process according to the invention, 1 mole of 5-nitro-3H-benzofuran-2-one is reacted with 1 to 5 moles of pentanoic anhydride, 0.1 to 2 moles of a salt of pentanoic acid, and 0 to 1.5 moles of pentanoic acid, then the resulting reaction mixture is acidified, and then the expected product is isolated, if desired.

Under other preferential conditions for carrying out the process according to the invention, one mole of 5-nitro-3H-benzofuran-2-one is reacted with two moles of pentanoic anhydride and one mole of a salt of pentanoic acid, then the resulting reaction mixture is acidified, then the expected product is isolated.

In the implementation of the process according to the invention, the salt of pentanoic acid may be a salt of sodium, potassium or of tertiary amine. This salt may be prepared extemporaneously, preferably in situ, from pentanoic acid and a base. The base may be sodium carbonate.

In the implementation of the process according to the invention, the resulting reaction mixture is brought into contact with an acid. This acid will be preferably dilute sulfuric acid; indeed, it permits better recovery of the expected final product.

Still under preferential conditions for carrying out the process, the crude product obtained may be recrystallised in an acid. This acid will be advantageously acetic acid.

The present invention also provides the use of the product corresponding to formula (I) or its tautomeric form (II) for the production of synthesis intermediates. In particular, it provides the production of [2-butyl-5-nitro-benzofuran-2-one] *2-butyl-5-nitro-benzofuran* which may act as an intermediate in the synthesis of an antiarrhythmic agent, dronedarone.

The examples below will permit a better understanding of the invention.

EXAMPLES

Example 1

The following are charged to a three-necked flask:

478.7 g (2.57 moles) of pentanoic anhydride 131.3 g (1.285 moles) of pentanoic acid 81.6 g (0.771 mole) of sodium carbonate 230 g (1.285 moles) of 5-nitro-3H-benzofuran-2-one and the mixture is raised to a temperature of 80° C. for a period of 6 hours, with stirring.

The mixture is cooled to 20° C. and the following are added gradually within 15 minutes:

377.8 g (0.771 mole) of sulfuric acid diluted to 20%.

The temperature of the mixture rises to about 40° C.

The suspension is then cooled to 20° C. and the precipitate is filtered. It is washed with 250 ml of deionised water then with 250 ml of heptane.

After oven drying under reduced pressure at 60° C., a crude product with a purity of 95% is obtained.

Pure 3-(1-hydroxy-pentylidene)-5-nitro-3H-benzofuran-2-one is obtained by recrystallisation in acetic acid.

The analysis of the product is as follows:

| | | | |
|---|---|---|---|
| Melting point: | | 164° C. (DSC) | |
| Elemental analysis (theoretical): | | C 59.1% (59.3%), H 5.0% (4.9%), N 5.4% (5.3%) | |
| NMR (H): | | 200 MHz | |
| Solvent: | | DMSO | |
| δ = 0.90 ppm | Triplet | J=7.1Hz | 3H |
| δ = 1.37 ppm | Multiplet | | 2H |
| δ = 1.60 ppm | Multiplet | | 2H |
| δ = 2.94 ppm | Triplet | J=7.9Hz | 2H |
| δ = 7.30 ppm | Doublet | $J_{H7-H6}$=8.9Hz | 1H |
| δ = 8.05 ppm | Quadruplet | $J_{H6-H7}$=8.9Hz; $J_{H6-H4}$=2.3Hz | 1H |
| δ = 8.38 ppm | Doublet | $J_{H4-H6}$=2.3Hz | 1H |

Example 2

The following are charged to a three-necked flask:

96 g (1.6 moles) of 100% acetic acid 49 g (0.2 mole) of 40% sulfuric acid 26.3 g (0.1 mole) of 3-(1-hydroxy-pentylidene)-5-nitro-3H-benzofuran-2-one.

The mixture is brought to reflux, with stirring, over a period of 8 hours, the internal temperature being in the vicinity of 116° C.

An orange-coloured solution is gradually obtained with the liberation of gas.

The solution is cooled to ambient temperature and 50 g of water are added, then the solution is extracted twice under hot conditions with 140 g of heptane.

The combined organic phases are treated with 250 g of water and the pH is adjusted to 8 by adding a 30% potash solution (about 20 ml), then the aqueous phase is drawn off.

The separated organic phase is then dried by azeotropic distillation of water then the solvent is removed by distillation and the resulting oil is heated under reduced pressure in order to remove the traces of solvent.

A slightly yellow oil which crystallises at ambient temperature is thus obtained.

The 2-butyl-5-nitrobenzofuran obtained has a purity (high pressure liquid chromatography by external standardisation with respect to a reference standard) greater than 98% and a residual amount of heptane, by vapour phase chromatography, of less than 1.5%.

The NMR (H) spectrum 200 MHz (solvent: DMSO) is as follows:

| | | | |
|---|---|---|---|
| δ = 0.90 ppm | Triplet | J=7.2Hz | 3H |
| δ = 1.35 ppm | Multiplet | | 2H |
| δ = 1.66 ppm | Multiplet | | 2H |
| δ = 2.80 ppm | Triplet | J=7.4Hz | 2H |
| δ = 6.80 ppm | Singlet | | 1H |
| δ = 7.70 ppm | Doublet | $J_{H7H6}$=9Hz | 1H |
| δ = 8.11 ppm | Doublet of doublet | $J_{H6H7}$=9Hz; $J_{H6H4}$2.3Hz | 1H |
| δ = 8.47 ppm | Doublet | $J_{H4H6}$2.3Hz | 1H |

What is claimed is:

1. A compound having the formula (I) or its ketonic tautomer form (II)

(I)

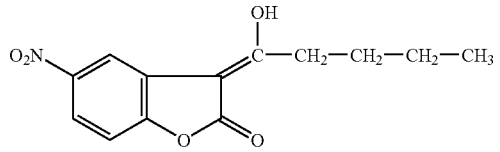

(II)

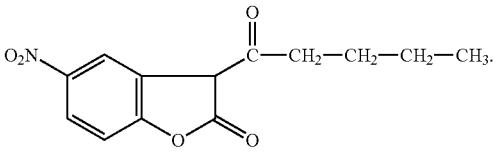

2. A compound having the formula I according to claim 1, which is 3(1-hydroxy-pentylidene)-5nitro-3H-benzofuran-2-one.

3. A compound to formula II according to claim 2 which is 3-(1-oxopentyl)-5-nitro-3H-benzofuran-2-one.

4. A process for the preparation of the compound having the formula (I) or (II), (I)

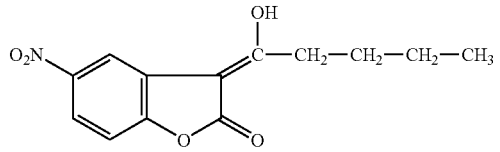

(II)

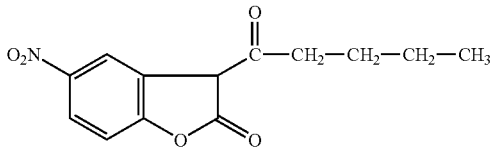

in which 5-nitro-3H-benzofuran-2-one is reacted, at a temperature above 30° C., with pentanoic anhydride and a salt of pentanoic acid, optionally in the presence of pentanoic acid, then the resulting reaction mixture is acidified, and then the above compound is isolated.

5. A process according to claim 4, in which 1 mole of 5-nitro-3H-benzofuran-2-one is reacted with 1 to 5 moles of pentanoic anhydride, 0.1 to 2 moles of a salt of pentanoic acid and 0 to 1.5 moles of pentanoic acid, then the resulting reaction mixture is acidified and then the above compound is isolated.

6. A process according to claim 4, in which 1 mole of 5-nitro-3H-benzofuran-2-one is reacted with 2 moles of pentanoic anhydride and 1 mole of a salt of pentanoic acid, then the resulting reaction mixture is acidified, and then the above compound is isolated.

7. A process according to claim 4, in which the salt of pentanoic acid is the salt of sodium, potassium or a salt of tertiary amine.

8. A [prowess] *process* according to claim 4, in which the salt of pentanoic acid is produced extemporaneously from pentanoic acid and a base.

9. A process according to claim 4, in which the salt of pentanoic acid is produced in situ from pentanoic acid and sodium carbonate.

10. A process according to claim 4, in which the reaction mixture is acidified with sulfuric acid.

11. A process according to claim 4, in which the above formula (I) or its tautomeric form (II) is purified by recrystallisation in acetic acid.

[12. Synthesis intermediate produced using the compound of formula (I) or of its tautomeric form (II) as claimed in claim 1.]

[13. 2-butyl-5-nitro-benzofuran-2-one produced using the compound of formula (I) or of its tautomeric form (II) as claimed in claim 1.]

* * * * *